United States Patent
Beer et al.

(10) Patent No.: US 8,338,166 B2
(45) Date of Patent: Dec. 25, 2012

(54) SORTING, AMPLIFICATION, DETECTION, AND IDENTIFICATION OF NUCLEIC ACID SUBSEQUENCES IN A COMPLEX MIXTURE

(75) Inventors: Neil R. Beer, Pleasanton, CA (US); Benjamin J. Hindson, Livermore, CA (US); Billy W. Colson, Jr., San Ramon, CA (US); Joseph P. Fitch, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1729 days.

(21) Appl. No.: 11/650,363

(22) Filed: Jan. 4, 2007

(65) Prior Publication Data

US 2008/0166793 A1  Jul. 10, 2008

(51) Int. Cl.
  *C12M 1/34* (2006.01)
  *C12M 3/00* (2006.01)
  *C12M 1/00* (2006.01)

(52) U.S. Cl. ............... 435/288.3; 435/283.1; 435/305.1; 435/305.2; 435/288.5; 435/288.4; 435/287.2

(58) Field of Classification Search ............... 435/283.1, 435/288.3, 305.1, 305.2, 288.5, 288.4, 287.2
  See application file for complete search history.

(56) References Cited

U.S. PATENT DOCUMENTS

| | | | |
|---|---|---|---|
| 5,498,392 A | 3/1996 | Wilding et al. | |
| 6,964,994 B1 | 11/2005 | Antonietti et al. | |
| 2002/0032242 A1 | 3/2002 | Antonietti et al. | |
| 2002/0055167 A1* | 5/2002 | Pourahmadi et al. | ...... 435/287.2 |
| 2002/0058332 A1 | 5/2002 | Quake et al. | |
| 2003/0175944 A1* | 9/2003 | Yang et al. | .................. 435/287.1 |
| 2004/0180346 A1 | 9/2004 | Anderson et al. | |
| 2004/0200909 A1 | 10/2004 | McMillan et al. | |
| 2004/0248167 A1 | 12/2004 | Quake et al. | |
| 2005/0032240 A1 | 2/2005 | Lee et al. | |
| 2005/0032729 A1 | 2/2005 | Shyamala | |
| 2005/0042597 A1 | 2/2005 | Pham | |
| 2005/0048581 A1* | 3/2005 | Chiu et al. | ..................... 435/7.1 |
| 2005/0084421 A1 | 4/2005 | Unger et al. | |
| 2005/0194316 A1 | 9/2005 | Pourahmadi et al. | |
| 2005/0221339 A1 | 10/2005 | Griffiths et al. | |

(Continued)

FOREIGN PATENT DOCUMENTS

WO  WO 2004/083443 A  9/2004

(Continued)

OTHER PUBLICATIONS

Williams, R., et al., "Amplification of complex gene libraries by emulsion PCR," Nature Methods, vol. 3, No. 7, Jul. 2006, pp. 545-550.

(Continued)

*Primary Examiner* — Nathan Bowers
(74) *Attorney, Agent, or Firm* — Eddie E. Scott

(57) ABSTRACT

A system for identifying all of the known and unknown pathogenic or non-pathogenic organisms in a sample. A droplet generator creates droplets from the sample. The droplets constitute sub-nanoliter volume reactors containing the organism sized particles. A lysis device performs lysis of the organisms to release the nucleic acids. An amplifier amplifies the nucleic acids. A fractionater releases the nucleic acids from the droplets. A parallel analyzer identifies all of the known and unknown pathogenic or non-pathogenic organisms in the sample.

28 Claims, 9 Drawing Sheets

U.S. PATENT DOCUMENTS

| | | | |
|---|---|---|---|
| 2005/0233314 A1 | 10/2005 | Juang et al. | |
| 2005/0239192 A1 | 10/2005 | Nasarabadi et al. | |
| 2005/0252773 A1 | 11/2005 | McBride et al. | |
| 2005/0266398 A1* | 12/2005 | Lea et al. | 435/5 |
| 2006/0057599 A1 | 3/2006 | Dzenitis et al. | |
| 2006/0084165 A1 | 4/2006 | Lee et al. | |
| 2007/0111302 A1* | 5/2007 | Handique et al. | 435/287.2 |
| 2008/0050804 A1* | 2/2008 | Handique et al. | 435/287.2 |
| 2008/0057572 A1* | 3/2008 | Petersen et al. | 435/306.1 |

FOREIGN PATENT DOCUMENTS

| | | | |
|---|---|---|---|
| WO | WO 2005/002730 A | 1/2005 | |
| WO | WO 2006/125458 A | 11/2006 | |

OTHER PUBLICATIONS

Diehl, F., et al, "BEAMing: single-molecule PCR on microparticles in water-in-oil emulsions," Nature Methods, vol. 3, No. 7, Jul. 2006, pp. 551-559.

Joanicot, M. et al., "Droplet Control for Microfluidics," Science, vol. 309, Aug. 5, 2005, pp. 887-888.

Musyanovych, A., et al., "Miniemulsion Droplets as single Molecule Nanoreactors for Polymerase Chain Reaction," Biomacromolecules, vol. 6, 2005, pp. 1824-1828.

Ksiazek, T.G., et al., "A Novel Coronavirus Associated with Severe Acute Respiratory Syndrome," The New England Journal of Medicine, V. 348, May 15, 2003, 16 pgs.

Leamon, J. H., et al., "Overview: methods and applications for droplet compartmentalization of biology," Nature Methods, vol. 3, No. 7, Jul. 2006, pp. 541-543.

He, M., et al., Selective Encapsulation of Single Cells and Subcellular Organelles into Picoliter- and Femtoliter-Volume Droplets, Anal. Chem., V. 77, 2005, pp. 1539-1544.

Nakano, M., et al., "Single-molecule PCR using water-in-oil emulsion," Journal of Biotechnology, 102, 2003, pp. 117-124.

* cited by examiner

SORTING, AMPLIFICATION, DETECTION, AND IDENTIFICATION OF NUCLEIC ACID SUBSEQUENCES IN A COMPLEX MIXTURE

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to sorting, amplification, detection, and identification and more particularly to sorting, amplification, detection, and identification of nucleic acid subsequences in a complex mixture.

2. State of Technology

United States Published Patent Application No. 2005/0032729 by Venkatakrishna Shyamala for identification of oligonucleotides for the capture, detection and quantitation of West Nile virus published Feb. 10, 2005 provides the following state of technology information: "The (Patent Application No. 2005/0032729) invention is based on the development of a sensitive, reliable nucleic acid-based diagnostic test for the detection of WNV in biological samples, particularly blood samples, from potentially infected subjects. The techniques described herein utilize extracted sample nucleic acid as a template for amplification of conserved genomic regions of the WNV sequence using transcription-mediated amplification (TMA), as well as in a 5' nuclease assay, such as the TaqMan® technique. The methods allow for the detection of as few as 10 copies of the target WNV sequence in viremic samples. Moreover, the methods described herein provide for a one-pot analysis wherein captured sample nucleic acids can be subjected to amplification and detection in the same container. Using the methods of the invention, infected samples can be identified and excluded from the blood supply for transfusion, as well as for the preparation of blood derivatives."

United States Published Patent Application No. 2005/0042597 for a Viral detection system by Thuy Diem Pham published Feb. 24, 2005 provides the following state of technology information: "RT-PCR based detection systems for avian leukosis/sarcoma virus in unfertilized chicken eggs have been developed. In this assay, the virus can be directly isolated from the egg albumen and the viral RNA efficiently screened by RT-PCR. The amplified RT-PCR product is then directly sequenced, in order to determine avian leukosis/sarcoma virus viral subgroup specificity. Systems specifically designed for effective detection of avian leukosis/sarcoma virus in chicken eggs have been refined, modifications of such systems for use in adult birds are also available. The combined use of RT-PCR and direct sequencing of the RT-PCR product provides a new approach for identifying ALSV-infected poultry. Hence, the present invention makes available molecular-based diagnostic methods for the rapid detection of ALSV retroviruses for use by the poultry industry and public health agencies."

United States Published Patent Application No. 2005/0233314 by Jyh-Lyh Juang et al for Sensitive and quantitative detection of pathogens by real-time nested PCR published Oct. 20, 2005 provides the following state of technology information: "The (Patent Application No. 2005/0233314) invention provides a method for detecting RNA or DNA pathogens in a sample. The (Patent Application No. 2005/0233314) invention also provides a method for quantifying RNA or DNA pathogens in a sample. Both methods comprise subjecting a sample suspected of containing an RNA or DNA pathogen, to real-time nested PCR. 'Real-time' detection allows one to measure the accumulation of amplified product during the course of the reaction, rather than simply analyzing the final product amount following the course of sequential cycles of amplification. 'Nested' PCR generally comprises a two-staged polymerase chain reaction process. In a first-stage polymerase chain reaction, a pair of 'outer' oligonucleotide primers are used to amplify a first nucleotide sequence. In a second-stage polymerase chain reaction, a second set of 'inner' or 'nested' oligonucleotide primers are used to amplify a smaller second nucleotide sequence that is contained within the first nucleotide sequence. In the methods of the invention, both stages of nested PCR are based on real-time amplification. The method of the invention is capable of detecting or quantifying less than 10 copies of RNA or DNA in a sample. The method of the invention may be used to detect or quantify SARS-CoV in a sample."

United States Published Patent Application No. 2006/0134609 by Jeffrey, M. Linnen et al for compositions and methods for determining the presence of SARS coronavirus in a sample published Jun. 22, 2006 provides the following state of technology information: "A novel coronavirus has been identified that causes serious disease in humans. The disease manifests itself with a constellation of clinical findings that have been named the 'severe acute respiratory syndrome' or 'SARS.' The virus was first identified in China and has shown potential to spread rapidly to other countries. There is no known treatment and there has been a high fatality rate among patients who have presented with pneumonia due to the virus. The signs and symptoms of SARS are common to many diseases. At present, isolation of the patient for periods of 10 days after resolution of disease is recommended to stem the spread of the disease.

The genome of SARS-CoV was recently sequenced and initial diagnostic tests have been developed, including tests to detect antibodies to the virus and polymerase chain reaction (PCR) assays to detect viral sequences. The antibody tests are inadequate because 10-14 days or more are required for antibodies to the virus to develop to detectable levels. The PCR tests initially developed appeared to be highly specific but were sensitive in only about 50% of suspected cases. These PCR tests all amplified a sequence located in the region from about nucleotide 15000 to nucleotide 19000 in the genome.

The low sensitivity of these initial PCR tests may have several causes. For example, the PCR primers may be cross-reacting with other sequences in the samples, thereby resulting in the production of unwanted amplification products. Also, the amount of nucleic acid from SARS-CoV may be below a threshold level of detection or inhibitors in the reaction mixture may be digesting the target nucleic acid or interfering with amplification and/or detection. In addition, because SARS-CoV contains genomic RNA, these initial PCR tests may be performing an inefficient reverse transcription step prior to amplification by PCR. Thus, a need exists for a method which allows for the rapid, sensitive and specific detection of SARS-CoV nucleic acid in a test sample. And for such a method to be of clinical significance, it should be capable of distinguishing the presence of SARS-CoV from that of human coronavirus strains 229E (HCoV-229E) and OC43 (HCoV-OC43), as these latter two viruses are responsible for about 30% of mild upper respiratory tract illnesses.

The (Patent Application No. 2005/0042597) invention relates to oligonucleotides useful for determining the presence of SARS coronavirus in a test sample. The oligonucleotides . . . may be incorporated into detection probes, capture probes and amplification oligonucleotides, or used in various combinations thereof."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

There are an estimated $10^{31}$ viruses on Earth, making them by far the most abundant biological entities. Identifying and measuring viruses in clinical or environmental sample is extremely challenging. Many viruses are impossible to culture, making traditional phenotypic characterization infeasible. Viruses, compared to micro-organisms and higher life forms, evolve rapidly (particularly RNA viruses) making large fractions of the genome susceptible to genetic drift and shift. It is not unusual for two descendent viruses that produce similar disease to have multiple mutations across the genomes. With no gene fidelity, profiling (including detection) cannot be accomplished using conserved sequences.

The present invention provides a sample analysis system capable of performing, singly or in combination, reagent and analyte mixing, cell lysing, nucleic acid amplification, optical detection and discrimination, and nucleic acid detection and characterization. A key component of the system is a chip-based device for sorting, amplification, detection, and identification of nucleic acid subsequences in a complex mixture.

One embodiment of the present invention provides an apparatus for identifying all of the known and unknown pathogenic or non-pathogenic organisms in a sample. The Merriam-Webster dictionary defines "organism" as: a complex structure of interdependent and subordinate elements whose relations and properties are largely determined by their function in the whole. The term organism includes viruses, bacteria, protozoa, microbes, and other pathogenic or non-pathogenic entities.

The organisms of the sample include nucleic acids. The apparatus includes a droplet generator for creating droplets from the sample. The droplets constitute sub-nanoliter volume reactors containing the organism sized particles. A lysis device performs lysis of the organisms to release the nucleic acids. An amplifier amplifies the nucleic acids. A fractionater releases the nucleic acids from the droplets. A parallel analyzer identifies all of the known and unknown pathogenic or non-pathogenic organisms in the sample. In one embodiment the parallel analyzer is a genomic analyzer. In another embodiment the parallel analyzer is a proteomic analyzer.

In one embodiment an apparatus utilizes micro-channels in a chip. The micro-channels provide a flow circuit. The micro-channels include initial processing channels and capillary electrophoresis (CE) lanes that provide analysis.

The present invention has many uses. For example the present invention can be used in biowarfare detection applications for identifying, detecting, and monitoring bio-threat agents that contain nucleic acid signatures, such as spores, bacteria, etc. The present invention has biomedical applications where it can be used for tracking, identifying, and monitoring outbreaks of infectious disease. The present invention can also be used for automated processing, amplification, and detection of host or microbial DNA in biological fluids for medical purposes including infectious disease diagnosis and treatment, cancer detection and monitoring, and pathology. The present invention has forensic applications and can be used for automated processing, amplification, and detection DNA in biological fluids for forensic purposes. The present invention has use for food and beverage safety and can be used for automated food testing for bacterial or viral contamination.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
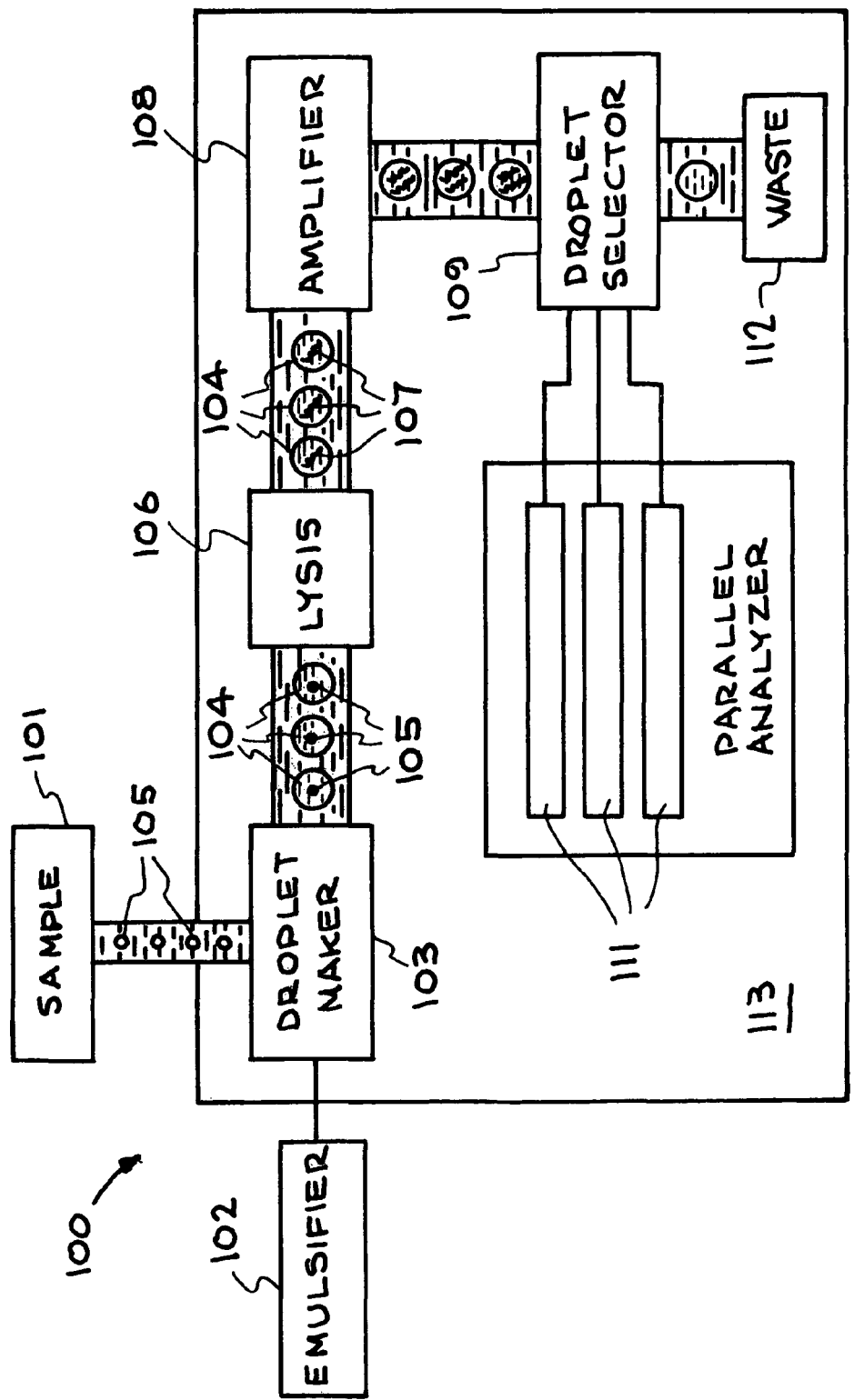
FIG. 1 illustrates one embodiment of an apparatus for identifying all of the known and unknown pathogenic or non-pathogenic organisms in a sample.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

In recent years, we have seen more deadly pathogens emerge from nature such as Ebola virus the causative agent of Hemorrhagic fever. Furthermore, existing pathogens are becoming much more virulent and less sensitive to existing treatments and genetic engineering techniques now enable the creation of potentially more deadly pathogens. One key delay in responding to these threats is the ability to rapidly isolate and genetically identify a known and unknown pathogen from a complex clinical or environmental sample. Currently available DNA-sequencing techniques, such as those used in the recent SARS response, allow analysis of newly discovered pathogens. These techniques, however, rely on early identification and isolation of the pathogen from complex and often diluted samples. Therefore samples with very large viral or bacterial loads are needed or the target agent must be cultured through multiple steps using growth patterns for isolation and amplification. There are human pathogens that are not amenable to culture.

It is well known that quarantine strategies are much more difficult and costly to implement once a disease has spread. Therefore, effective response to a terrorist attack using a pathogen similar in virulence and contagion to the 1918 flu will require surveillance and characterization 10 to 100 times more rapid than was accomplished in the outstanding and unprecedented international response to SARS.

Referring now to the drawings and in particular to FIG. 1, one embodiment of an apparatus for identifying all of the known and unknown pathogenic or non-pathogenic organisms in a sample wherein the organisms include nucleic acids is illustrated. The apparatus is designated generally by the reference numeral 100. The apparatus 100 identifies substantially all of the known and unknown pathogenic or non-pathogenic organisms in the sample.

The apparatus 100 provides capillary electrophoresis (CE) lanes 111 on a chip 113. As shown in FIG. 1, a sample 101 is directed into the apparatus 100. The sample 101 contains known and unknown pathogenic or non-pathogenic organisms 105. The sample 101 is prepared to contain primers, probes, and dNTPs. An emulsifier 102 is added to the sample 101.

The portion of the chip 113 wherein the sample 101 and the emulsifier 102 come together forms a droplet maker 103. The sample 101 and the emulsifier 102 are injected into the flow channels generating the droplet which constitute isolated mobile PCR reactors. The droplet maker 103 creates droplets 104 from the sample 101. The droplets 104 constitute sub-nanoliter volume reactors containing organism sized particles 105. The droplets 104 are created within emulsified shells by forcing them through an appropriately sized mechanical orifice in the droplet maker 103. This may be accomplished using microfluidic T-junctions, microjet, inkjet, pin systems, or other ways of creating droplets.

A device 106 provides lysis of the organisms 105 to release the nucleic acids 107. The lysis device 106 is an optical window for delivering light. Additionally, chemical agents in the droplets may also be used to induce lysis. Individual droplets 104 are irradiated to lyse cells using the optical window in the lysis device 106. Lysis of the organisms 105 releases the nucleic acids 107. Lysis can also be performed by droplet heating, in which case the optical window may be replaced by a resistive, conductive, or radiative heating element.

An amplifier 108 amplifies the organisms 105. The nucleic acids 107 have been released from the organisms 105 and the nucleic acids 107 are amplified using the amplifier 108. For example, the amplifier 108 can be a thermocycler. The nucleic acids 107 can be amplified in-line before arraying them. As amplification occurs, detection of fluorescence-labeled TaqMan type probes occurs if desired. Following amplification, the system does not need decontamination due to the isolation of the chemical reactants.

A droplet selector 109 identifies droplets with amplified nucleic acid and directs them to further analysis while allowing empty droplets to pass to waste 112. Amplified droplets then release their nucleic acids 110 into the analysis channels of the parallel analyzer 111. The organisms 105 are arranged for parallel analysis in the parallel analyzer 111. Selected droplets 104 may be assigned to one of the many available CE channels 111 for electrophoretic separation characterization. Voltage actuation of channel electrodes and acoustic, magnetic, or optical actuation may be employed to force the droplets 104 into the analysis channel 111. In another embodiment, overlaid high pressure pads may combine with electrostatic potential to force the droplets 104 into the CE channel 111 for characterization if the device substrate is PDMS or another suitable polymer. Waste is directed to the waste reservoir 112. All organisms 105 in the sample 101 are analyzed by the apparatus 100. This can be accomplished by a genomic analyzer and/or a parallel physical/proteomic analyzer.

In various embodiments, the apparatus 100, and particularly the chip 113, is manufactured by different processes. In one embodiment, the apparatus 100 is manufactured by a photolithography process utilizing a wet etch in glass or borosilicate of the bottom and top layers which are then aligned and bonded together. Individual devices are then cut from the bonded wafers on the diamond saw. In another embodiment, the apparatus 100 is manufactured by a photolithography process utilizing a front and backside Deep Reactive Ion Etch (DRIE) process where the front side of a Si wafer contains the microfluidic channels and the back side etch creates the fluid vias to connect to the channel. The front side is then sealed by anodic bonding of the borosilicate, or glass, cover layer, and the chip is cut on the diamond saw. In another embodiment, the apparatus 100 is manufactured by a lithography process where SU-8 photoresist is patterned into a positive-relief of the channel architecture using the standard photolithography process. This patterned structure then becomes a mold for the addition of liquid Polydimethylsiloxane (PDMS) which is flowed over the SU-8 and cured. The elastomeric, cured PDMS is then pulled from the mold. A glass coverslip is spin coated with a small layer of PDMS and cured. The 2 layers (glass plus PDMS with channels) are then brought together and cured such that the PDMS forms a complete seal around the channel geometry. Fluidic ports are then cored out of the polymeric PDMS.

The structural details of an apparatus for identifying all of the known and unknown pathogenic or non-pathogenic organisms in a sample having been described, the method of operation of the apparatus 100 will now be considered. The method of operation of the apparatus 100 includes a series of steps. In the first step the sample 101 is processed to isolate organism sized particles. The sample 101 is also processed by adding primers, probes, and dNTPs. An emulsifier 102 is added to the sample 101.

The portion of the apparatus 100 wherein the sample 101 and the emulsifier 102 are injected forms a droplet maker 103. The droplet maker 103 creates droplets 104 from the sample 101 wherein the droplets 104 constitute sub-nanoliter volume reactors containing organism sized particles 105. Lysis 106 of the organisms 105 releases the nucleic acids 107. The organisms 105 are amplified by amplifier 106. The nucleic acids 107 have been released from the organisms and the nucleic acids 107 are amplified using amplification techniques.

The droplets 104 are fractionated or formatted by the droplet splitter 103 to release the amplified nucleic acids 107. This can be accomplished by releasing amplified nucleic acids 107 from each droplet 104 or by dissolving/disrupting the emulsification shells of the droplets 104. The organisms 105 are arranged for parallel analysis. This is accomplished by the parallel analyzer 111. All organisms 105 in the sample 101 are analyzed. This accomplished by a genomic analyzer and/or a physical/proteomic analyzer.

The apparatus 100 can be used in clinical applications for identification of known and unknown respiratory illnesses, unknown causes of death, drug efficacy testing, and other identification. The apparatus 100 can be used in medical surveillance for identification of new and emerging infectious disease such as SARS. The apparatus 100 can be used for identification of genetically modified biological threats. The apparatus 100 can also be used for identification of environmental biological background characterization for planning, response, forensics, and attribution.

Figure 2:
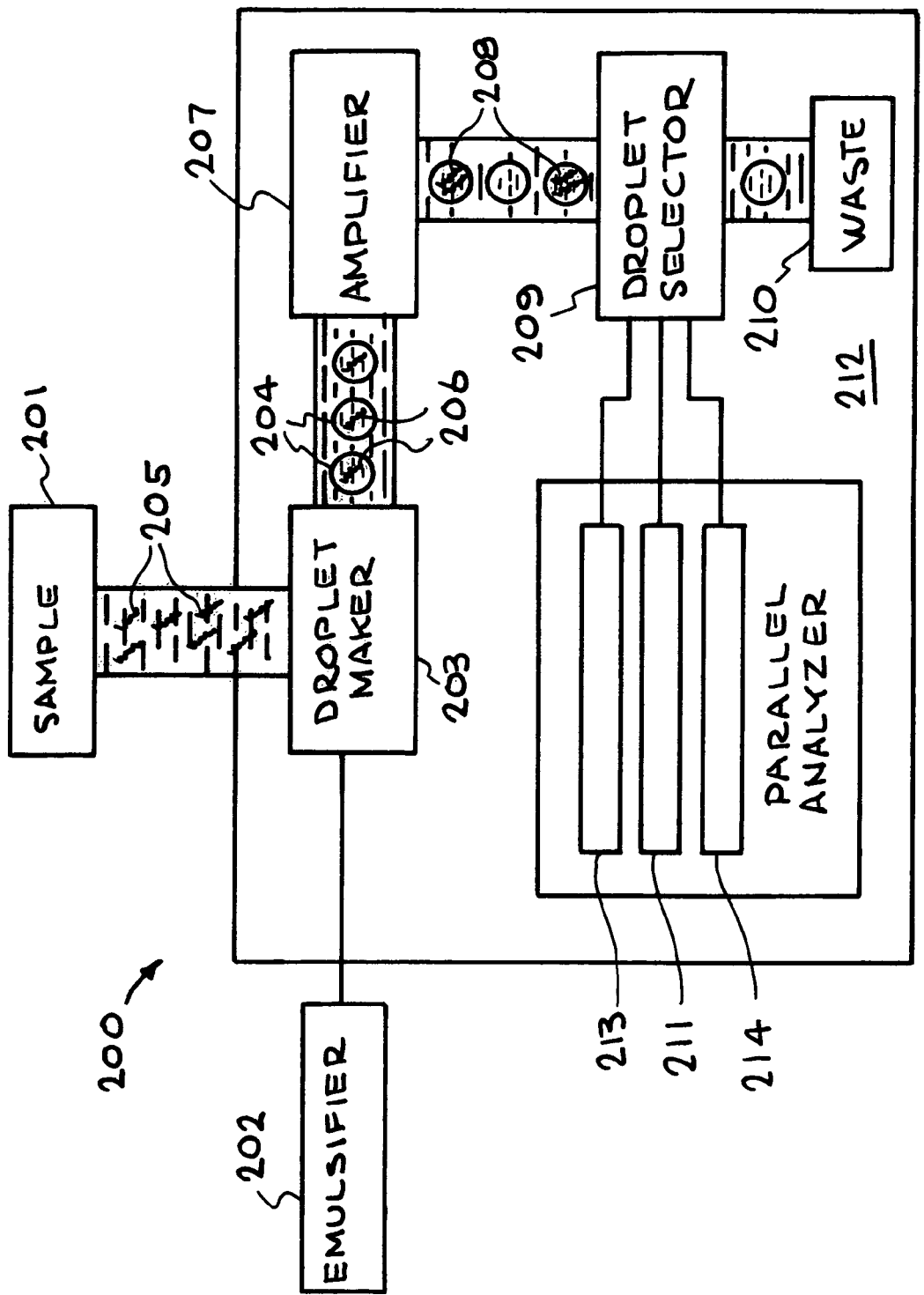
FIG. 2 illustrates another embodiment of an apparatus for identifying all of the known and unknown pathogenic or non-pathogenic organisms in a sample.

Referring now to FIG. 2, another embodiment of an apparatus for identifying all of the known and unknown pathogenic or non-pathogenic organisms in a sample wherein nucleic acid from the organisms is illustrated. The apparatus is designated generally by the reference numeral 200. The apparatus 200 identifies substantially all of the known and unknown pathogenic or non-pathogenic organisms in the sample.

The apparatus 200 utilizes micro-channels 211, 213, and 214 in a chip 212. The micro-channels 213 and 211 provide a flow circuit. The micro-channels 213 provide initial processing and the capillary electrophoresis (CE) lanes 211 and 214 provide analysis.

A complex environmental or clinical sample 201 is prepared using known physical (ultracentrifugation, filtering, diffusion separation, electrophoresis, cytometry etc.), chemical (pH), and biological (selective enzymatic degradation) techniques to extract and separate target nucleic acids or intact individual particles 205 (e.g., virus particles) from background (i.e., intra- and extra-cellular RNA/DNA from host cells, pollen, dust, etc.). This sample, containing relatively purified nucleic acid or particles containing nucleic acids (e.g., viruses), can be split into multiple parallel channels and mixed with appropriate reagents required for reverse transcription and subsequent PCR (primers/probes/dNTPs/enzymes/buffer). Each of these mixes are then introduced into the system in such a way that statistically no more than a single RNA/DNA is present in any given microreactor. For example, a sample containing $10^6$ target RNA/DNA would require millions of microreators to ensure single RNA/DNA distribution. As shown in FIG. 2, the sample 201 is directed into the apparatus 200. The sample 201 contains known and unknown pathogenic or non-pathogenic organisms 205. An emulsifier 202 is added to the sample 201.

The apparatus 200 utilizes a Microreactor Generator System (MGS). The MGS system performs analyte mixing and injection, sample isolation, and system decontamination functions. Although multiple embodiments of the MGS system can be used in the apparatus 200, there are several key components, including: a hydrophobic carrier fluid, a fluid propulsion and metering device (typically a syringe pump), a fluidic channel with a T or cross junction forcing the dispersion of the analyte and reagent aqueous solution into the hydrophobic carrier fluid, a multi-port selection valve for channel priming, and a variable width main channel for controlling droplet spacing and velocity. The pump is used to draw and pump fluids through the flow circuit.

The hydrophobic carrier fluid provides the medium for translating the pump movements into fluid motion and for creating the spherical droplets that serve as the micron-scale reactors. This occurs due to the immiscibility of the hydrophilic droplets within the hydrophobic flow, as the sheared aqueous fluid relaxes into a spherical form to minimize surface tension (by minimizing surface area). Continuous flow of both the hydrophobic carrier fluid and the aqueous reagent fluid ensures both the production and separation of the microscale reactors, eliminating the chance of cross-contamination.

The performance characteristics of the pump allow for precise and accurate metering of the flow rates which determine droplet size under the relation:

$$D_{droplet} \cong \frac{\sigma D_{hydraulic}^3}{\mu Q_o} \qquad D_{hydraulic} = \frac{4 \times \text{Area}}{\text{Perimeter}}$$

where Dh is the hydraulic radius of the channel at the junction, $Q_0$ is the volumetric flow rate in m3/s, σ is the surface tension in kg/s2, μ is the viscosity in kg/(m*s).

The aqueous inlet channel serves to mix various assay components (i.e., analyte, oligonucleotides, primer, probe, enzymes etc.) in preparation for amplification and detection. This prevents contamination of the syringe pump, and is easily decontaminated by rinsing with buffer. The channel geometry allows for dividing the sample into multiple aliquots for subsequent analysis serially or in parallel with multiple streams. The scalability of the architecture allows for multiple different reactions to be tested against aliquots from the same sample. Decontamination by flushing the channels dilute solution of sodium hypochlorite, followed by deionized water could also be used.

The portion of the chip 212 wherein the sample 201 and the emulsifier 202 come together forms a droplet generator or droplet maker 203. The sample 201 and the emulsifier 202 are injected into the flow channels generating the droplets which constitute isolated mobile PCR reactors. The droplet maker 203 creates droplets 204 from the sample 201. The droplets 204 constitute sub-nanoliter volume reactors containing organism sized particles 206. The droplets 204 are created within emulsified shells by forcing them through an appropriately sized mechanical orifice in the droplet maker 203. This may be accomplished using microfluidic T-junctions, microjet, inkjet, pin systems, or other ways of creating droplets.

An amplifier 207 provides Nucleic Acid Amplification. This may be accomplished by the Polymerase Chain Reaction (PCR) process, an exponential process whereby the amount of target DNA is doubled through each reaction cycle utilizing a polymerase enzyme, excess nucleic acid bases, primers, catalysts (MgCl2), etc. The reaction is powered by cycling the temperature from an annealing temperature whereby the primers bind to single-stranded DNA (ssDNA) through an extension temperature whereby the polymerase extends from the primer, adding nucleic acid bases until the complement strand is complete, to the melt temperature whereby the newly-created double-stranded DNA (dsDNA) is denatured into 2 separate strands. Returning the reaction mixture to the annealing temperature causes the primers to attach to the exposed strands, and the next cycle begins.

The heat addition and subtraction powering the PCR chemistry on the amplifier device 207 is described by the relation:

$$Q = hA(T_{wall} - T_\infty)$$

The amplifier 207 amplifies the organisms 206. The nucleic acids 208 have been released from the organisms 206 and the nucleic acids 208 are amplified using the amplifier 207. For example, the amplifier 207 can be a thermocycler. The nucleic acids 208 can be amplified in-line before arraying them. As amplification occurs, detection of fluorescence-labeled Taq- Man type probes occurs if desired. Following amplification, the system does not need decontamination due to the isolation of the chemical reactants.

Initial concentration of targeted organisms will be unknown, and can vary over many orders of magnitude. For this reason many droplets will be generated that will contain no genetic material to amplify. The proposed sorting system will advantageously only select the droplets that have a sufficient quantity of post-amplified nucleic acid material to characterize. This is performed by the interrogation of each droplet by an orthogonal laser beam or LED, to excite fluorescent reporters supplied to each droplet in the reagent mix. This could be an intercalating dye that only fluoresces when bound to double stranded nucleic acids such as segments of PCR product. The fluorescent reporter could also be a Taqman type FRET probe. A detector senses the fluorescence if applicable and reports to the controller the presence of a "hot" droplet. This droplet, moving along the centerline of the flow channel is then selected for characterization by capillary electrophoresis and/or archival. Other types of luminescence techniques could be used for optical droplet discrimination, including chemiluminescence or bioluminescence which do not require an external excitation source simplifying instrumentation design and have inherently low back-ground emission for highly sensitive detection. Addition of this droplet selector component 209 greatly simplifies the design of the instrument, since it greatly reduces the number of parallel capillary electrophoresis or electrophoresis channels that are necessary to characterize the selected amplicons. In one embodiment droplets selected for electrophoresis will be sorted to the electrophoresis channel by optical trapping while the "empty" droplets move on to waste. In another embodiment, droplets selected for electrophoresis will be sorted to the electrophoresis channel by pneumatic valve actuation to transfer the droplet to another channel while the rest of the droplets continue to waste. In another embodiment, droplets selected for electrophoresis will be sorted to the electrophoresis channel by magnetic attraction to transfer the droplet to another channel while the rest of the droplets continue to waste 210. In another embodiment, droplets selected for electrophoresis will be sorted to the electrophoresis channel by acoustic pressure from a piezoelectric transducer to transfer the droplet to another channel while the rest of the droplets continue to waste.

Optical Detection is provided under the relation:

$$l = \frac{\ln\left(\frac{VC_{p,i}\varepsilon}{n_i^2 r_F t f_{NA} \eta}\right) + 57.97}{\ln 4}$$

The apparatus 200 employs an optical window (described subsequently) to the flow channels 213, 211, and 214 to provide for detection and analysis of the droplet contents in the parallel analyzer such as capillary electrophoresis.

A fractionater or droplet splitter releases the amplified nucleic acids by opening the droplets and releasing the amplified nucleic acids. The organisms are arranged for parallel analysis in the parallel analyzer. Selected droplets may be assigned to one of the many available CE channels for electrophoretic characterization. Capillary electrophoresis is provided under the relation:

$$t = \frac{L^2}{(\mu_{cph} + \mu_{co})V}$$

$$\mu_{co} \approx \frac{\varepsilon\zeta}{(4\pi\eta r_{capillary})}$$

Voltage actuation of channel electrodes and acoustic, magnetic, or optical actuation may be employed to force the droplets into the CE channel. In another embodiment, overlaid high pressure pads may combine with electrostatic potential to force the droplets into the CE channel for characterization. Waste is directed to the waste reservoir. All organisms in the sample are analyzed by the apparatus. This can be accomplished by a genomic analyzer and/or a parallel physical/proteomic analyzer.

There are multiple different methods for characterizing the amplified PCR product. In one embodiment, real-time detection of amplified nucleic acid sequences is accomplished using optical-based assays that either increase or decrease the emission from fluorescence-labeled probes during each amplification step. One technique for real-time PCR is TaqMan, a homogeneous PCR test that uses a fluorescence resonance energy transfer probe. This probe typically contains a "reporter" dye at the 5' end and a "quencher" dye at the 3' end. Intact, there is very little fluorescent emission from the probe, since the proximity of the quencher to the reporter dye serves to suppress the reporter emission. During PCR amplification, the probe anneals to a targeted complementary amplicon strand and begins extending one of the primers. An enzyme, (Taq polymerase) cleaves the probe and displaces both dye molecules, allowing them to separate and diffuse into the surrounding fluid. The resulting increase in reporter emission can be monitored and correlated PCR product concentration.

This apparatus 200 provides for nucleic acid characterization for novel or unknown viruses and bacteria by microcapillary, capillary, or gel electrophoresis due to the ability to interface with an electrophoresis system. The apparatus 200 maintains the presence of an array of selectable, independently programmable capillary electrophoresis (CE) lanes on the chip or orthogonal to it running perpendicular to the main channel flow. As selected droplets pass above open CE channels, flow can be slowed and an electric potential fired on the CE electrodes causing migration of the droplet of interest through the port in the main flow channel and into the CE channel. In one embodiment, the droplet can be captured by electrostatic attraction alone. In another embodiment, a combination of electrostatic attraction and mechanical actuation can be combined to capture individual droplets. (Mechanical actuation is controlled by overlaying pressurized gas lines in an orthogonal pattern above and parallel to the CE channels which, when pressurized, flex the cover layer of the device above the open port, deflecting the hydrophobic cover toward the droplet, which is repulsed downward into the open port.) In another embodiment the droplet may be bifurcated prior to CE channel entrance to allow for a fraction of the droplet to be carried downstream to an archival aspiration port. In another embodiment a combination of electrostatic and magnetic force may be employed to move the droplets into the CE channels. In another embodiment, a combination of acoustic pressure from piezoelectric transducers and electrostatic attraction may be used to move the droplets into the channel. In another embodiment, a combination of optical pressure from an integrated optical trap may be used to with electrostatic force to move droplets into the channel.

An applied potential field in the electrophoresis channels attracts the nucleic acid fragments and separates them according to their charge to size ratio due to the presence of an appropriate molecular sieve. The sieve acts to retard the nucleic acid flow. Because of this action the differing lengths of nucleic acids become separated into bands as they migrate with solvent ions along the electrophoresis channel. This art describes a system that will then image the CE channels to detect the fluorescence of tagged nucleic acid bands as they migrate down the channels. In a preferred embodiment the system contains multiple CE channels in parallel with a charge coupled device (CCD) imaging system detecting the banding patterns.

To perform calibration of the electrophoresis channels a few of the droplets will be seeded with nucleic acid "Ladders," sequences of different lengths that vary by a constant number of bases. These "ladders" when amplified in PCR and run on some of the device's electrophoresis channels will ensure that the PCR reagent mixing, thermal heating, and electrophoretic separation are functioning appropriately on the device. Furthermore, since multiple flow channels can be run in parallel, an entire flow channel can be employed to run only calibration and control nucleic acids. These controls will serve as "fiducials" to provide a banded image useful in diagnosing and confirming device performance.

Characterizing the products generated by the polymerase chain reaction can give information about the target genome that was amplified. The PCR reaction can be designed to generate specific products, or amplicons, with distinct sizes (i.e., lengths, number of bases). Electrophoresis can be used to separate PCR products according to size. It is important to have size reference standards that can be used for calibrating the electrophoresis process.

DNA ladders or size reference standards can be incorporated into individual droplets and transported to the electrophoresis system. They could also be directly injected into the electrophoresis system.

A synthetic virus construct such as armored RNA can be used as an end-to-end system control and would very closely mimic the behavior of real virus or biological particle that could be present in the sample. It can be spiked to the sample or added in line. The control would provide information of sample addition, mixing, droplet formation, reagent addition, extraction, sample purity, sample preparation, particle lysis, reverse transcription, PCR amplification and detection. The control could have its own set of PCR primers and could either co-exist in a droplet with the target or in its own droplet. The PCR primers for the control can be designed to generate products that have distinct sizes that cover the range and resolution required to identify and characterize electropherograms from targets, essentially generating size ladders or reference standards in situ. The sequence target used for calibration can be made synthetically so that the products can be used as sequencing controls or other down stream characterization processes. The control can also yield information regarding any loss of specificity or sensitivity of the device.

In another embodiment, droplets can be barcoded and tracked as they are transported throughout each module of the system. Barcoding can be done with particles, such as beads, crystals, and identified using fluorescence, spectral signature or other unique signature identifiers. Barcodes can be made from unique combinations of particles, or an array of uniquely identifiable particles. Their size could be tailored (micrometers to nanometers) and the materials can be inert so as not to affect performance of the system or the assays. If droplets need to be manipulated, such as split one droplet into 2, the identity of the original droplet can be tracked and correlated with results from different (parallel) detection platforms.

Figure 3A:
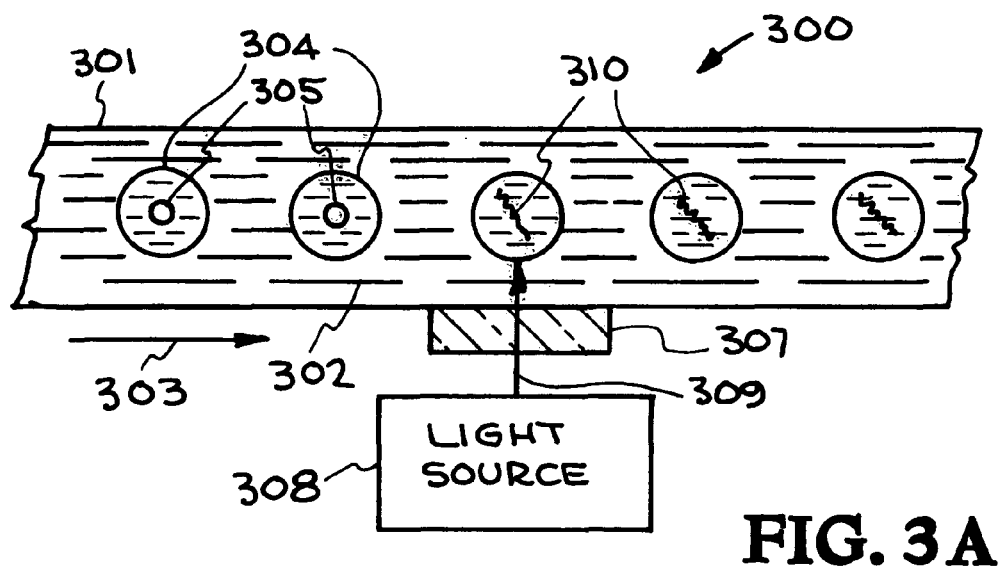
FIGS. 3A and 3b illustrate two embodiments of lysising devices.
Figure 3B:
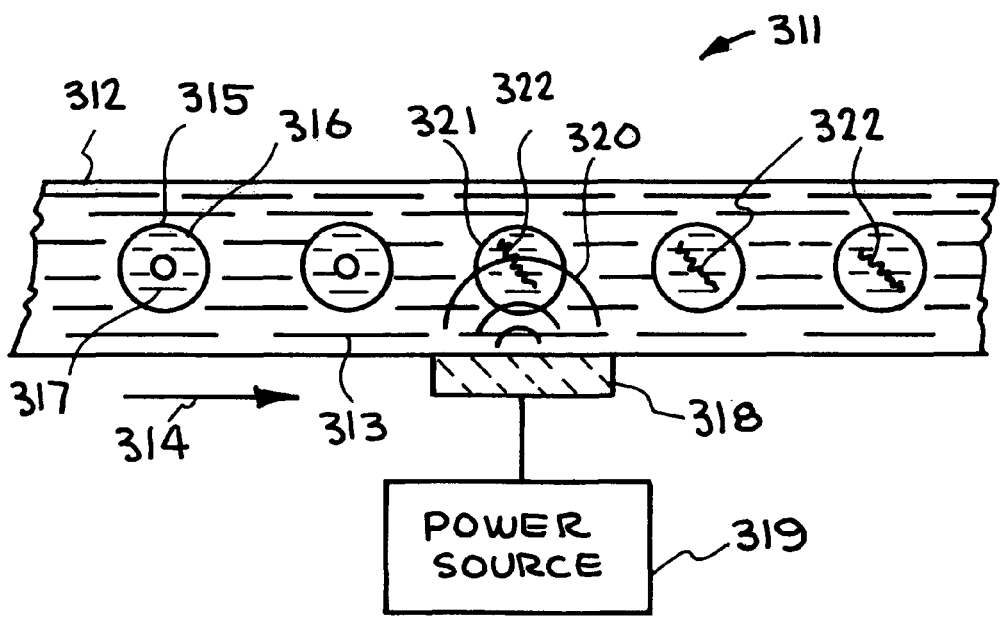

Referring now to FIGS. 3A and 3B, embodiments of the lysis device is illustrated. The lysis device provides lysis of the organisms to release the nucleic acids. The embodiments of FIGS. 3A and 3B will be described in greater detail.

Referring now to FIG. 3A, one embodiment of the lysis device is shown and designated generally by the reference numeral 300. The lysis device 300 includes a micro-channel 301 with fluid 302 that provides a flow circuit flowing in the direction indicated by the arrow 303. A complex environmental or clinical sample has been formed into individual droplets 304 which constitute isolated mobile PCR reactors. The sample droplets 304 contain known and unknown pathogenic or non-pathogenic organisms 305 and a fluid 306.

The device 300 provides lysis of the organisms 305 to release the nucleic acids. The lysis device 300 includes an optical window 307. A light source 308 such as a laser produces a light or laser beam 309 that is directed through the optical window 307. The light or laser beam 309 directs electromagnetic radiation to generate a plasma that creates a shock wave inside the droplets 304 sufficient to lyse the bacterial cell wall or protein capsids, releasing target nucleic acids (RNA and DNA) 310 within the droplets 304.

The individual droplets 304 are irradiated to lyse cells using the optical window 307 in the lysis device 300. Lysis of the organisms 305 releases the nucleic acids 310. Lysis of the organisms 305 can also be achieved by radiative heating from the laser 308 and laser beam 309. Lysis of the organisms 305 can also be achieved using ultrasound-generating piezoelectric actuators in place of the laser 308 to focus acoustic pressure on the cell walls. Lysing is necessary to make the nucleic acids accessible to the reagents used for amplification and or detection.

Referring now to FIG. 3B, another embodiment of the lysis device is shown and designated generally by the reference numeral 311. The lysis device 311 includes a micro-channel 312 with fluid 313 that provides a flow circuit flowing in the direction indicated by the arrow 314. A complex environmental or clinical sample has been formed into individual droplets 315 which constitute isolated mobile PCR reactors. The sample droplets 304 contain known and unknown pathogenic or non-pathogenic organisms 316 and a fluid 317.

The device 311 provides lysis of the organisms 316 to release the nucleic acids. The lysis device 311 includes a window 318. Lysis of the droplets 315 is achieved using an ultrasound-generating piezoelectric actuator or power source 319 to focus acoustic pressure 320 on the cell walls 321. Lysing is necessary to make the nucleic acids 322 accessible to the reagents used for amplification and or detection.

Resistive or conductive heating may also be used to lyse the organisms 316. In this case, a resistive heater 318 or Peltier device 318 is used to heat the droplets 315, instead of using a piezoelectric actuator. Lysing is necessary to make the nucleic acids 322 accessible to the reagents used for amplification and or detection.

The structural details of an apparatus for identifying all of the known and unknown pathogenic or non-pathogenic organisms in a sample having been described in connection with FIGS. 1, 2, 3A and 3B, the method of operation of the apparatus will now be considered. The method of operation of the apparatus includes a series of steps. In the first step the sample is processed to isolate organism sized particles. The sample is also processed by adding primers, probes, and dNTPs. An emulsifier is added to the sample.

The portion of the apparatus wherein the sample and the emulsifier are injected forms a droplet generator. The droplet maker creates droplets from the sample wherein the droplets constitute sub-nanoliter volume reactors containing organism sized particles. Lysis of the organisms releases the nucleic acids. The organisms are amplified by amplifier. The nucleic acids have been released from the organisms and the nucleic acids are amplified using amplification techniques.

The droplets are fractionated or formatted to release the amplified nucleic acids. This can be accomplished by releasing amplified nucleic acids from each droplet or by dissolving/disrupting the emulsification shells of the droplets. The organisms are arranged for parallel analysis. This is accomplished by the parallel analyzer. All organisms in the sample are analyzed. This accomplished by a genomic analyzer and/or a physical/proteomic analyzer.

The apparatus can be used in clinical applications for identification of unknown respiratory illnesses, unknown causes of death, drug efficacy testing, and other identification. The apparatus can be used in medical surveillance for identification of new and emerging infectious disease such as SARS. The apparatus can be used for identification of genetically modified biological threats. The apparatus can also be used for identification of environmental biological background characterization for planning, response, forensics, and attribution.

Figure 4A:
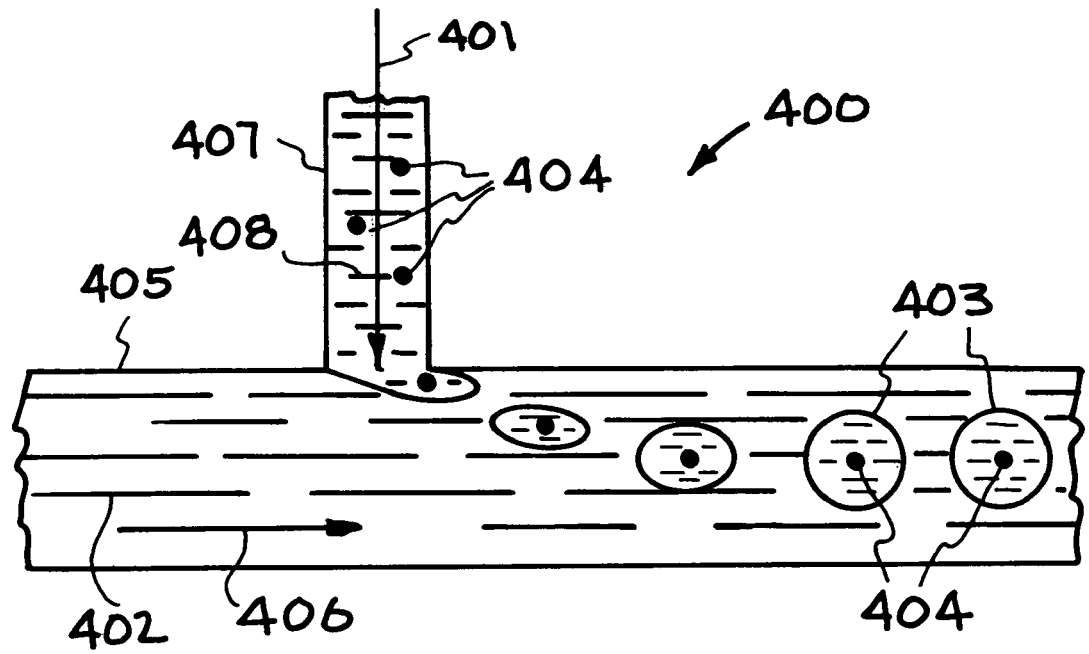
FIGS. 4A and 4B illustrate systems and methods of forming droplets.
Figure 4B:
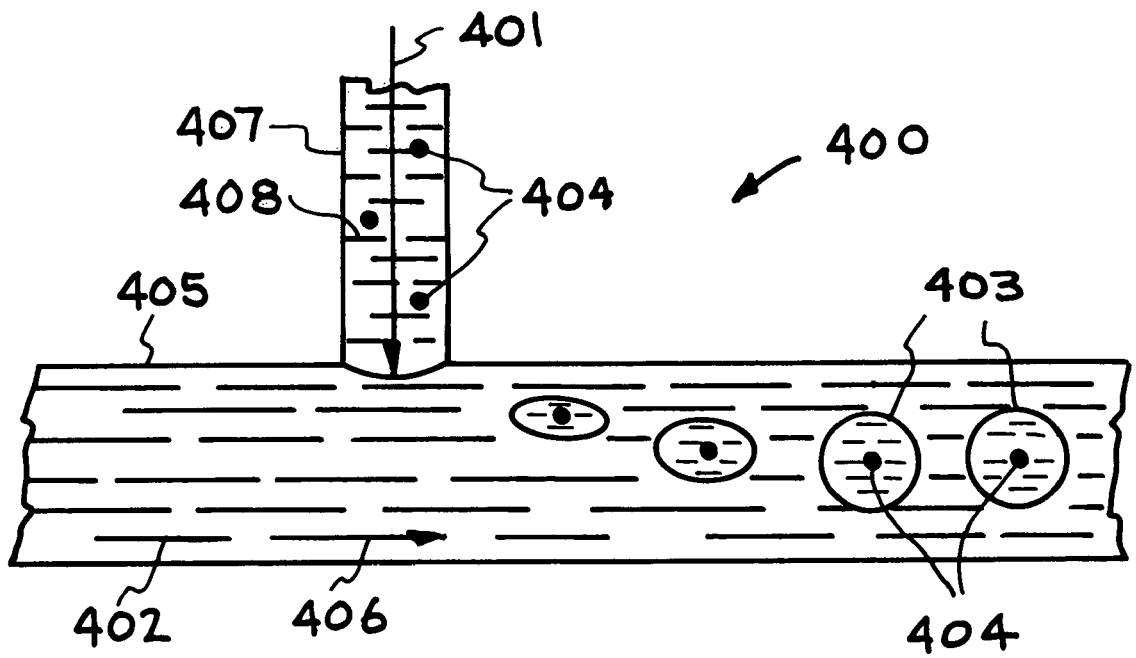

Referring to FIGS. 4A and 4B, a system and method of forming droplets is illustrated. FIGS. 4A and 4B illustrates the portion of the chip wherein the sample 401 and the emulsifier 402 come together to form a droplet generator or droplet maker. The droplet generator or droplet maker is designated generally by the reference numeral 400. The sample 401 and the emulsifier 402 generate droplets 403 which constitute isolated mobile PCR reactors. The droplet maker 400 creates the droplets 403 from the sample 401. The droplets 403 constitute sub-nanoliter volume reactors containing organism sized particles 404.

The emulsifier 402 flows in a flow channel 405 in the direction indicated by the arrow 406. The sample 401 is directed into the flow channel 405 by the droplet maker 400 by a sample channel 407. The organism sized particles 404 are carried in the sample channel 407 by a fluid 404. The droplet maker 400 creates the droplets 403 from the sample 401 and the droplets contain the organism sized particles 404. The droplets 403 constitute isolated mobile PCR reactors.

As shown in FIG. 4A, some of the aqueous solution 408 containing a pathogen or organism 404 is drawn into the flow of emulsifier 402 and eventually breaks free of the sample channel 407. The aqueous solution 408 containing a pathogen or organism 404 becomes a spherical droplet 403 as it is carried in the flow channel 405.

As shown in FIG. 4B, after the droplet 403 has been formed it is entrained in the flow of emulsifier 402. The aqueous solution 408 in the sample channel 407 is ready to start forming another droplet.

Figure 5:
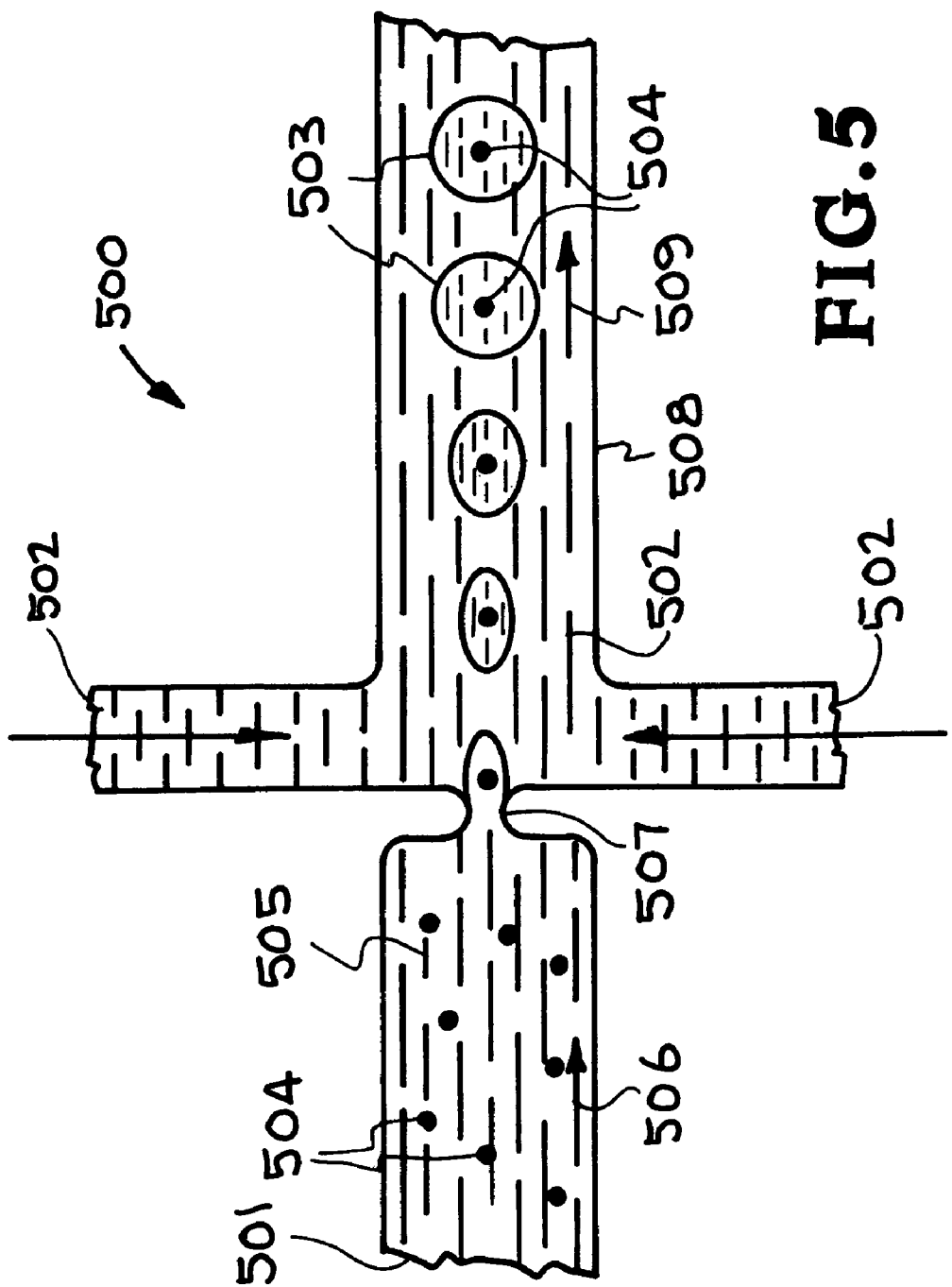
FIG. 5 shows another system and method of forming droplets.

Referring to FIG. 5 another embodiment of a system and method of forming droplets is illustrated. This embodiment is designated generally by the reference numeral 500. FIG. 5 illustrates the portion of the chip wherein the sample 501 and the emulsifier 502 come together to form the droplet generator or droplet maker 500. The sample 501 and the emulsifier 502 generate droplets 503 which constitute isolated mobile PCR reactors. The droplet maker 500 creates the droplets 503 from the sample 501. The droplets 503 constitute sub-nanoliter volume reactors containing organism sized particles 504.

As shown in FIG. 5 the aqueous solution 505 containing pathogens 504 flows in a sample channel 505 as indicated by the arrow 506. The aqueous solution 505 containing the organisms or pathogens 504 is forced through an orifice 507. A portion of the aqueous solution 505 containing the organisms or pathogens 504 breaks off and eventually becomes a spherical droplet 503 as it is carried in the flow channel 508. After the droplet 503 has been formed it is entrained in the flow of emulsifier 502 as indicated by the arrow 509. The droplet maker 500 creates the droplets 503 from the sample 501 and the droplets contain the organism sized particles 504. The droplets 503 constitute isolated mobile PCR reactors.

Figure 6B:
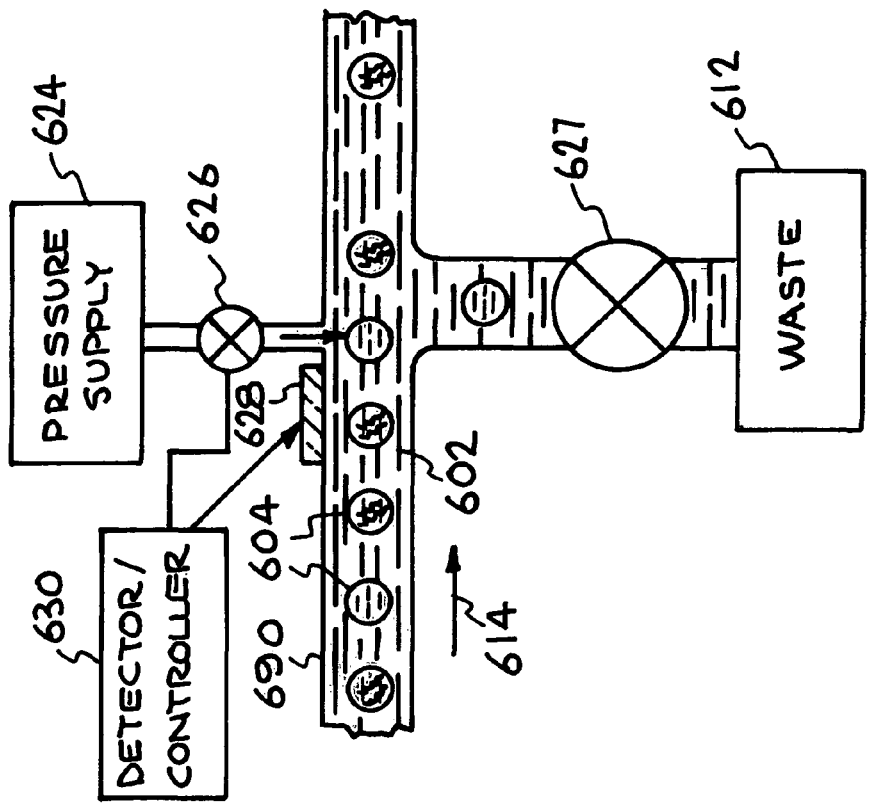
FIGS. 6A and 6B show systems and methods of shunting rejected droplets to waste.
Figure 6A:
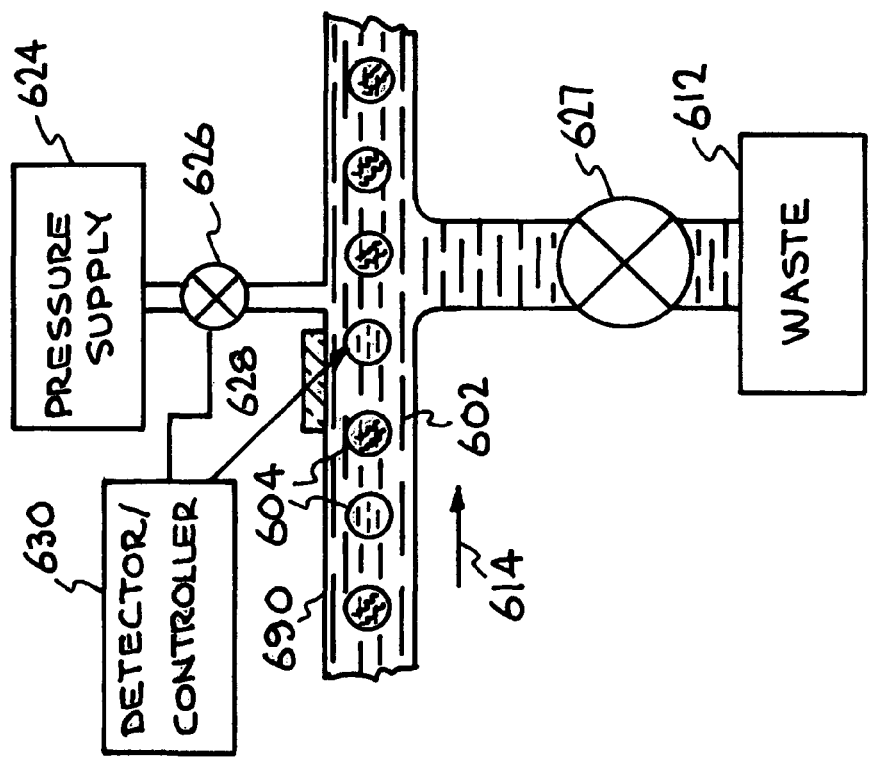

Referring now to FIGS. 6A and 6B, a system and method of shunting rejected droplets to waste is illustrated. As shown in FIG. 6A a micro-channel 690 with droplets 604 is illustrated. Some of the droplets contain nucleic acid 604 and some do not contain the nucleic acid. The droplets 604 are entrained in the emulsifier 602 and flow in the direction of arrow 614. As the droplets 604 pass by window 628 a detector/controller 630 determines which droplets are to be shunted to waste 612.

FIG. 6B show that a droplet that does not contain any nucleic acid has been detected. The detector/controller 620 opens the valves 626 and 627 and a puff from the pressure source 624 sends the rejected droplet into a conduit that leads to the waste receptacle 612.

Figure 7:
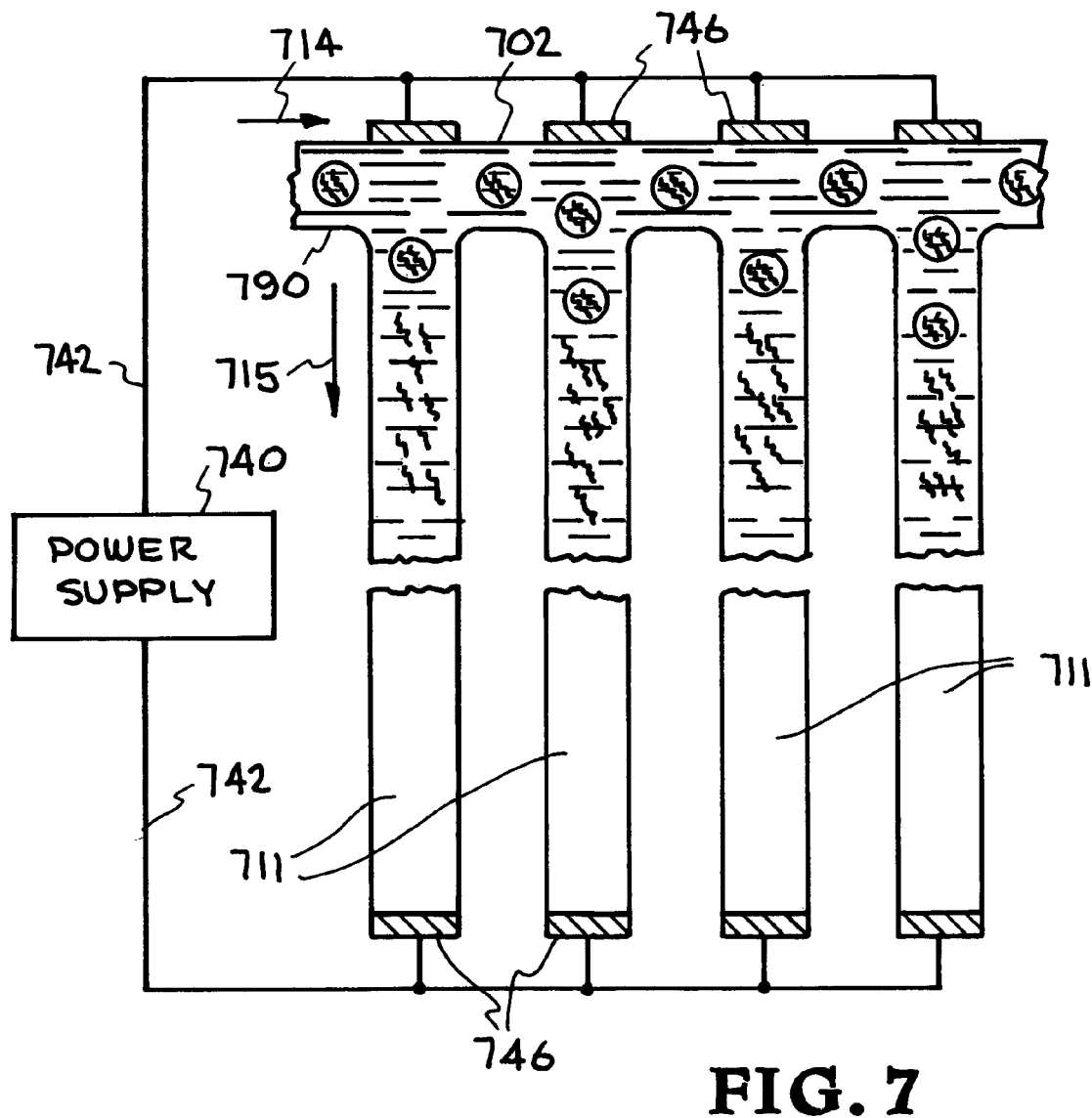
FIG. 7 illustrates a system and method for directing droplets into the analyzer channels.

Referring now to FIG. 7, a system and method for directing droplets into the analyzer channels is illustrated. A micro-channel 790 with emulsifier 702 and entrained droplets of nucleic acid moves in the direction of arrow 714. A power supply 740 and circuit 742 with contacts 746 create a field that causes the droplets to move in the direction of arrow 715 and into the analyzer channels 711.

Figure 8A:
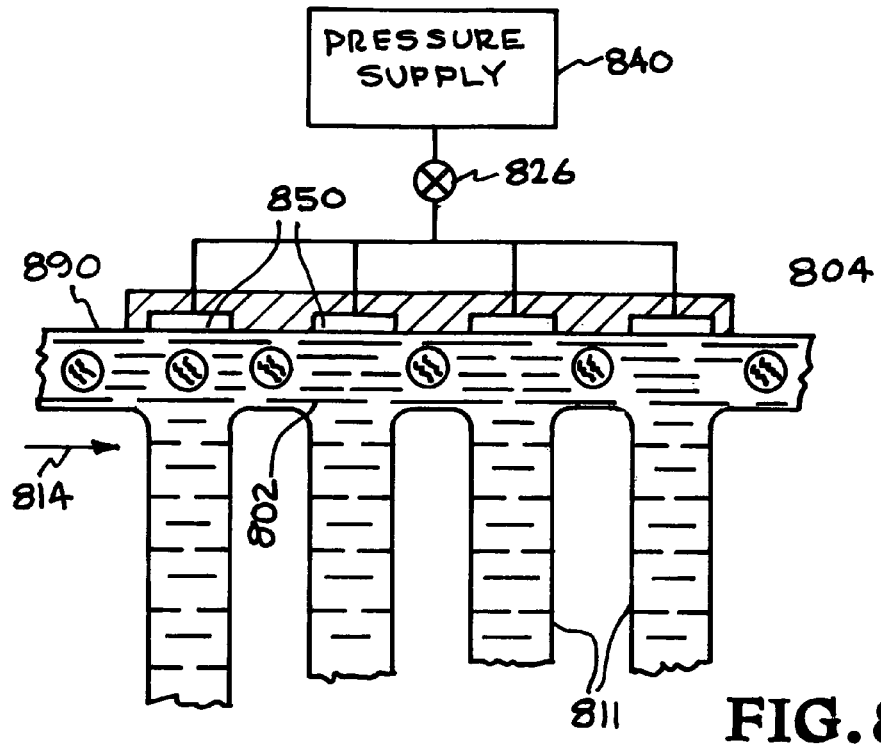
FIGS. 8A and 8B illustrate another system and method for directing droplets into the analyzer channels.
Figure 8B:
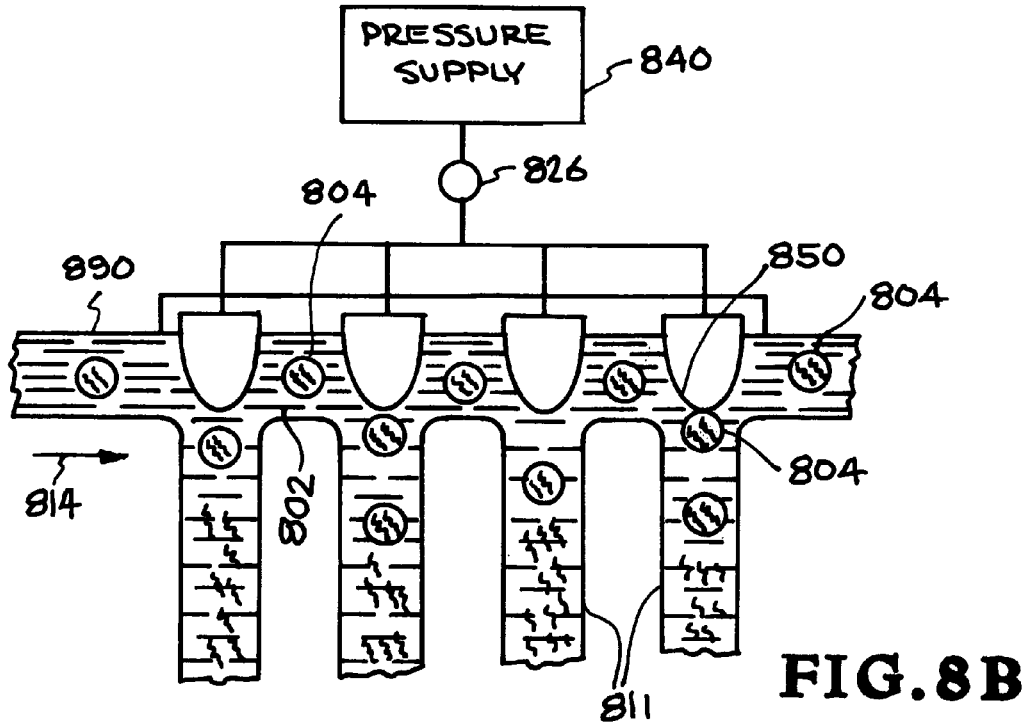

Referring now to FIGS. 8A and 8B, another system and method for directing droplets into the analyzer channels is illustrated. FIG. 8A shows micro-channel 890 with droplets 804 entrained in emulsifier 802 moving slowly in direction of arrow 814. A pressure supply 840 is shown with conduits connected to flexible areas 850 of the micro-channel covering. When valve 826 is opened, pressure distorts the micro-channel covering and the droplets 804 are forced into the analyzer channels 811 where the droplets can be dissolved to release the nucleic acid.

Figure 9A:
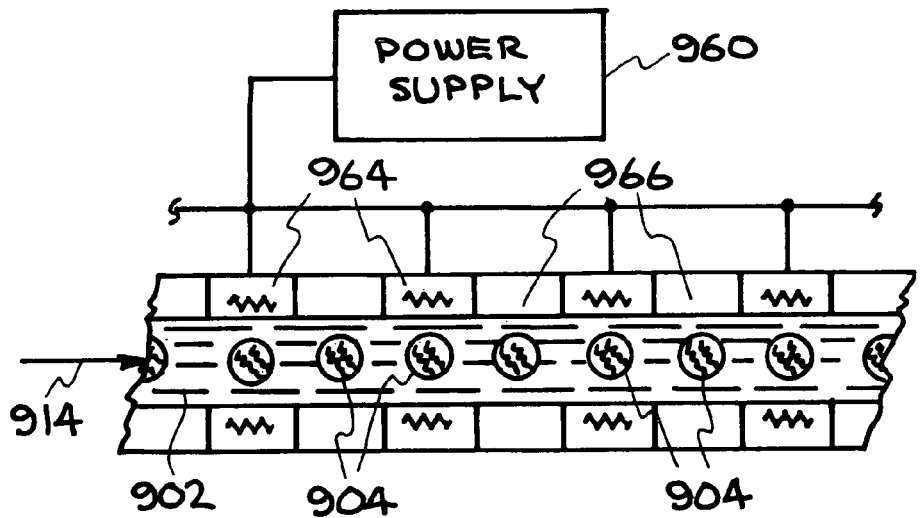
FIGS. 9A and 9B illustrate two systems and methods of amplifying the nucleic acid into the droplets using PCR.
Figure 9B:
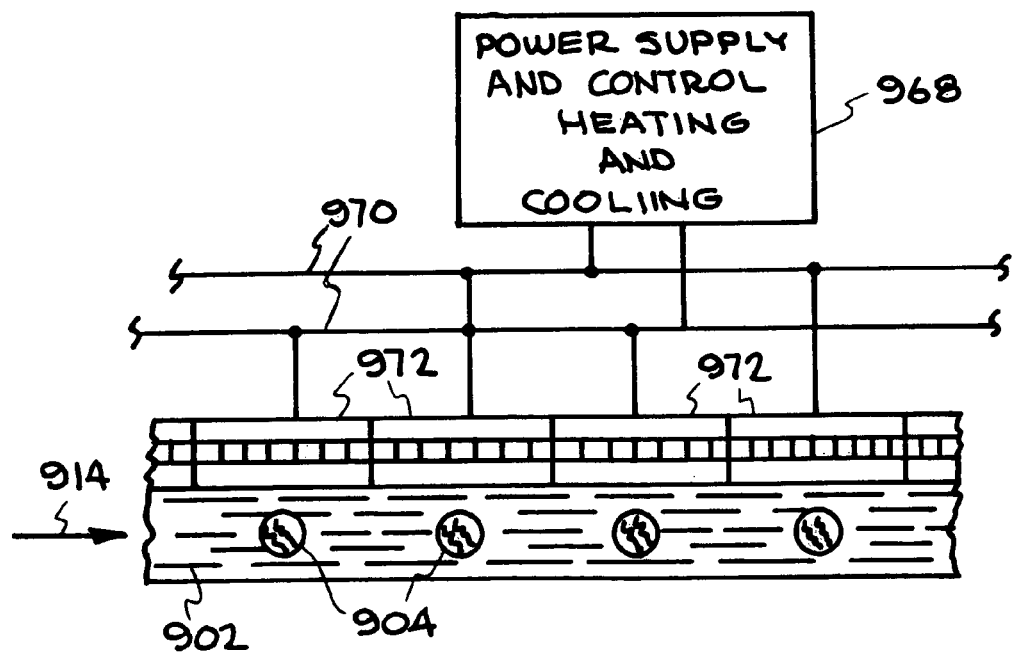

Referring now to FIGS. 9A and 9B, two systems and methods of amplifying the nucleic acid into the droplets using PCR are illustrated. Part of the PCR reaction is to alternately heat and cool the material to be replicated so in FIGS. 9A and 9B methods and systems for heating and cooling the droplets are illustrated. FIG. 9A shows droplets 904 in emulsifier 902 traveling in the direction of arrow 914 while in micro-channel 990 the droplets will pass through alternate heating 964 and cooling 966 zones. A power supply 960 provides power to the resistance heater and cooling zones. This can be accomplished with a cooling liquid or gas. FIG. 9B shows the droplets passing by thermo-electric units 972 which are powered and controlled by unit 968 and circuit 970. Thermo-electric units are Peltier devices that can both heat and cool.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for identifying the known and unknown pathogenic or non-pathogenic organisms in a sample wherein the organisms include nucleic acids, comprising:

a microfluidic flow channel,
an emulsifier source that directs an emulsifier into said microfluidic flow channel,
a droplet generator that directs the sample into said emulsifier and creates discrete droplets from the sample wherein said droplets constitute sub-nanoliter volume reactors containing the organisms;
a lysis device for performing lysis of the organisms to release the nucleic acids;
an amplifier for amplifying the nucleic acids;
a fractionater that releases the nucleic acids from said droplets; and
a parallel analyzer for identifying all of the known and unknown pathogenic or non-pathogenic organisms in the sample.

2. The apparatus for identifying all of the known and unknown pathogenic or non-pathogenic organisms in a sample of claim 1 wherein said droplet generator comprises a mechanical orifice and the sample is forced through said mechanical orifice into said emulsifier in said microfluidic flow channel creating said discrete droplets and wherein said discrete droplets have emulsified shells.

3. The apparatus for identifying all of the known and unknown pathogenic or non-pathogenic organisms in a sample of claim 1 wherein said lysis device comprises an optical window.

4. The apparatus for identifying all of the known and unknown pathogenic or non-pathogenic organisms in a sample of claim 1 wherein said lysis device comprises a laser for directing electromagnetic radiation through an optical window.

5. The apparatus for identifying all of the known and unknown pathogenic or non-pathogenic organisms in a sample of claim 1 wherein said lysis device comprises an ultrasound-generating piezoelectric actuator.

6. The apparatus for identifying all of the known and unknown pathogenic or non-pathogenic organisms in a sample of claim 1 wherein said lysis device comprises a wire-based ultrasound-generator inside the microchannel.

7. The apparatus for identifying all of the known and unknown pathogenic or non-pathogenic organisms in a sample of claim 1 wherein said lysis device comprises a resistive, conductive, or radiative heater that causes lysis through hyperthermia of the target organism.

8. The apparatus for identifying all of the known and unknown pathogenic or non-pathogenic organisms in a sample of claim 1 wherein said amplifier comprises a thermocycler.

9. The apparatus for identifying all of the known and unknown pathogenic or non-pathogenic organisms in a sample of claim 1 wherein said parallel analyzer comprises an electrophoresis system that includes capillary electrophoresis lanes.

10. The apparatus for identifying all of the known and unknown pathogenic or non-pathogenic organisms in a sample of claim 1 wherein said parallel analyzer comprises a capillary electrophoresis system.

11. The apparatus for identifying all of the known and unknown pathogenic or non-pathogenic organisms in a sample of claim 1 wherein said parallel analyzer comprises a genomic analyzer.

12. The apparatus for identifying all of the known and unknown pathogenic or non-pathogenic organisms in a sample of claim 1 wherein said parallel analyzer comprises a direct sequencer.

13. An apparatus for identifying all of the known and unknown pathogenic or non-pathogenic organisms in a sample wherein the organisms include nucleic acids, comprising:
a chip,
a microfluidic flow channel in said chip,
an emulsifier source directing an emulsifier into said microfluidic flow channel,
a droplet generator in said microfluidic flow channel that directs the sample into said emulsifier and creates discrete droplets from the sample wherein said droplets constitute sub-nanoliter volume reactors containing the organisms;
a lysis device in said microfluidic flow channel for performing lysis of the organisms to release the nucleic acids;
an amplifier in said microfluidic flow channel for amplifying the nucleic acids;
a fractionater in said microfluidic flow channel that releases the nucleic acids from said droplets; and
a parallel analyzer connected to said microfluidic flow channel for identifying all of the known and unknown pathogenic or non-pathogenic organisms in the sample.

14. The apparatus for identifying all of the known and unknown pathogenic or non-pathogenic organisms in a sample of claim 13 wherein said droplet generator comprises a mechanical orifice and the sample is forced through said mechanical orifice into said emulsifier in said microfluidic flow channel creating said discrete droplets and wherein said discrete droplets have emulsified shells.

15. The apparatus for identifying all of the known and unknown pathogenic or non-pathogenic organisms in a sample of claim 13 wherein said lysis device comprises an optical window.

16. The apparatus for identifying all of the known and unknown pathogenic or non-pathogenic organisms in a sample of claim 13 wherein said lysis device comprises a laser for directing electromagnetic radiation through an optical window.

17. The apparatus for identifying all of the known and unknown pathogenic or non-pathogenic organisms in a sample of claim 13 wherein said lysis device comprises an ultrasound-generating piezoelectric actuator.

18. The apparatus for identifying all of the known and unknown pathogenic or non-pathogenic organisms in a sample of claim 13 wherein said amplifier comprises a thermocycler.

19. The apparatus for identifying all of the known and unknown pathogenic or non-pathogenic organisms in a sample of claim 13 wherein said parallel analyzer comprises an electrophoresis system.

20. The apparatus for identifying all of the known and unknown pathogenic or non-pathogenic organisms in a sample of claim 13 wherein said parallel analyzer comprises a capillary electrophoresis system that includes capillary electrophoresis lanes.

21. The apparatus for identifying all of the known and unknown pathogenic or non-pathogenic organisms in a sample of claim 13 wherein said parallel analyzer comprises a genomic analyzer.

22. The apparatus for identifying all of the known and unknown pathogenic or non-pathogenic organisms in a sample of claim 13 wherein said parallel analyzer comprises a direct sequencer.

23. The apparatus for identifying all of the known and unknown pathogenic or non-pathogenic organisms in a sample of claim 13 including an optical detector connected to said microfluidic flow channel for analysis of the known and unknown pathogenic or non-pathogenic organisms in the sample.

24. The apparatus for identifying all of the known and unknown pathogenic or non-pathogenic organisms in a sample of claim 13 wherein said chip comprises a multiplicity of wafers produced by a wet etch in glass or borosilicate and wherein said wafers are then aligned and bonded together to produce bonded wafers.

25. The apparatus for identifying all of the known and unknown pathogenic or non-pathogenic organisms in a sample of claim 24 wherein said bonded wafers are then cut by a diamond saw to produce said chip.

26. The apparatus for identifying all of the known and unknown pathogenic or non-pathogenic organisms in a sample of claim 24 including a borosilicate or glass cover layer positioned over said microfluidic flow channel wherein said chip comprises a multiplicity of wafers produced by a photolithography process utilizing a front and backside Deep Reactive Ion Etch (DRIE) process where the front side of a Si wafer contains said microfluidic channel and the back side etch creates the fluid vias to connect to said microfluidic channel and said front side of said Si wafer is then sealed by anodic bonding of said borosilicate or glass cover layer to said front side of said Si wafer.

27. The apparatus for identifying all of the known and unknown pathogenic or non-pathogenic organisms in a sample of claim 13 wherein said chip comprises a multiplicity of wafers produced by a soft lithography process where SU-8 photoresist is patterned into a positive-relief on a channel architecture using a standard photolithography process and said patterned structure becomes a mold for the addition of liquid polydimethylsiloxane which is flowed over the SU-8 and cured.

28. The apparatus for identifying all of the known and unknown pathogenic or non-pathogenic organisms in a sample of claim 27 wherein said cured polydimethylsiloxane (PDMS) is then pulled from the mold, a glass coverslip is spin coated with a small layer of polydimethylsiloxane and cured, layers of glass plus PDMS with channels are brought together and cured such that the polydimethylsiloxane forms a complete seal around the channel geometry and fluidic ports are cored out of the polymeric polydimethylsiloxane.

* * * * *